(12) United States Patent
Besterman et al.

(10) Patent No.: US 6,608,046 B1
(45) Date of Patent: Aug. 19, 2003

(54) β-LACTAMASE AND DD-PEPTIDASE INHIBITORS

(75) Inventors: Jeffrey M. Besterman, Baie d'Urfe (CA); Jubrail Rahil, Dollard des Ormeaux (CA); Rex Pratt, Portland, CT (US)

(73) Assignee: MethylGene, Inc., St. Laurent (CA)

(*) Notice: Subject to any disclaimer, the term of this patent is extended or adjusted under 35 U.S.C. 154(b) by 0 days.

(21) Appl. No.: 09/582,255

(22) PCT Filed: Dec. 23, 1998

(86) PCT No.: PCT/US98/27518

§ 371 (c)(1), (2), (4) Date: Sep. 1, 2000

(87) PCT Pub. No.: WO99/33850

PCT Pub. Date: Jul. 8, 1999

Related U.S. Application Data

(60) Provisional application No. 60/068,837, filed on Dec. 24, 1997.

(51) Int. Cl.[7] ............ A61K 31/661; A61K 31/662; C07F 9/02
(52) U.S. Cl. ............ 514/120; 558/79; 568/12; 423/302; 423/316
(58) Field of Search ............ 514/120; 423/302, 423/316; 568/12; 558/79

(56) References Cited

FOREIGN PATENT DOCUMENTS

| EP | 260241 | * | 3/1988 |
| WO | 9113891 | * | 9/1991 |
| WO | 9221702 | * | 12/1991 |

OTHER PUBLICATIONS

Ramirez et al., Phosphorus Sulfur (1978), 4(1) pp. 43–46.*
Kang et al., Misaengmul Hakhoechi (1991), 29(6) pp. 353–360.*
Goto et al., Sep. Sci. Technol. (1995), 30(1) pp. 89–99.*
Cha et al., Bull Korean Chem. Soc. (1994), 15(11), pp. 1001–1003.*
Li, N. et al., "Structure–activity Studies of the Inhibition of Serine.Beta–Lactamases by Phosphonate Monoesters" Bioorg. Med. Chem.; 1997; vol. 5 (9); pp 1783–1788.
Laird R.M. et al., "Mechanism of Acyl Phosphonate Reactions. I. Kinetics of the Solvolyses of Benzoyl and p–Toluoyl Phenylphosphonates in Aqueous Dioxane" J. Chem. Soc., Perkin Trans. 2 (JCPKBH); 1973; (10); pp 1434–1436.
Kazlauskas R.J. et al., "Synthesis of Methoxycarbonyl Phosphate, New Reagent Having High Phosphoryl Donor Potential for Use in ATP Cofactor Regeneration" J. Org. Chem; 1985; vol. 50 (7); pp 1069–1076.
Li, Naixin, "Inhibition of Serine β–Lactamases by Acyl Phosphonates: a New Source of Inert Acyl and Phosphyl Enzymes" J. of the American Chemical Society; vol. 120, No. 18; May 1998; pp 4264–4268.
Pratt, R.F., "Salicyloyl Cyclic Phosphate, a Penicillin–Like Inhibitor of β–Lactamases" J. of the American Chemical Society, vol. 120, No. 13, Apr. 1998; pp 3004–3006.
Song, Y. et al., "Benzylpenicillin Methyl Phosphate. A Penicillin Prodrug That Inactivates RTEM.beta–Lactamase" Bioorg. Med. Chem. Lette.; 1994; vol. 4 (10) pp 1225–1228.
Rahil, J. et al., "Phosphonate Monoester Inhibitors of Class A. Beta–Lactamases" Biochem; 1991; vol. 275 (3) pp 793–795.

* cited by examiner

*Primary Examiner*—Taofiq Solola
(74) *Attorney, Agent, or Firm*—Keown & Associates

(57) ABSTRACT

The invention provides novel β-lactamase inhibitors, which are structurally unrelated to the natural product and semi-synthetic β-lactamase inhibitors presently available, and which do not possess β-lactam pharmacophore. These new inhibitors are fully synthetic, allowing ready access to a wide variety of structurally related analogs. Certain embodiments of these new inhibitors also bind bacterial DD-peptidases, thus potentially acting both as β-lactamase inhibitors and as antibiotics.

6 Claims, No Drawings

β-LACTAMASE AND DD-PEPTIDASE INHIBITORS

This application claims benefit of provisional application 60/068,837 Dec. 24, 1997.

BACKGROUND OF THE INVENTION

1. Field of the Invention

The invention relates to bacterial antibiotic resistance. More particularly, the invention relates to compositions and methods for overcoming bacterial antibiotic resistance.

2. Description of the Related Art

Bacterial antibiotic resistance has become one of the most important threats to modern health care. Cohen, Science 257:1051–1055 (1992) discloses that infections caused by resistant bacteria frequently result in longer hospital stays, higher mortality and increased cost of treatment. Neu, Science 257:1064–1073 (1992) discloses that the need for new antibiotics will continue to escalate because bacteria have a remarkable ability to develop resistance to new agents rendering them quickly ineffective.

The present crisis has prompted various efforts to elucidate the mechanisms responsible for bacterial resistance. Coulton et al. Progress in Medicinal Chemistry 31:297–349 (1994) teach that the widespread use of penicillins and cephalosporins has resulted in the emergence of β-lactamases, a family of bacterial enzymes that catalyze the hydrolysis of the β-lactam ring common to presently used antibiotics. More recently, Dudley, Pharmacotherapy 5: 9S14S (1995) has disclosed that resistance mediated by β-lactamases is a critical aspect at the core of the development of bacterial antibiotic resistance.

Attempts to address this problem through the development of β-lactamase inhibitors have had limited success. Sutherland, Trends Pharmacol Sci 12: 227–232 (1991) discusses the development of the first clinically useful β-lactamase inhibitor, clavulanic acid, which is a metabolite of *Streptomyces clavuligerus*. Coulton et al. (supra) disclose two other such semi-synthetic inhibitors, sulbactam and tazobactam presently available. Coulton et al. (supra) also teach that in combination with β-lactamase-susceptible antibiotics, β-lactamase inhibitors prevent antibiotic inactivation by β-lactamase enzymes, thereby producing a synergistic-effect against β-lactamase producing bacteria.

Rahil and Pratt, Biochem J. 275: 793–795 (1991), and Li et al., Bioorg. Med. Chem. 5: 1783–1788 (1997), teach that β-lactamase enzymes are inhibited by phosphonate monoesters. Song and Luger, Bioorg. Med. Chem. Lett., 4,1225–1228 (1994), teaches that *E. coli* RTEM β-lactamase is inhibited by benzylpenicillin methyl phosphate.

Laird and Spence, J.C.S. Perkin Trans. II 1434 (1973), Kazlauskas and Whitesides, J. Org. Chem. 50, 1069–1076 (1985), Chantrenne, Compte. Rend. Trav. Lab. Carlsberg Ser. Chim. 26: 297 (1948), and Marecek and Griffith, J. Am. Chem. Soc. 92: 917–921 (1970), report synthesis and solvolysis studies of acyl phosphate and acyl phosphonate compounds. Kluger et al., Can J. Chem., 74: 2395–2400 disclose that aminoacyl phosphates are useful as biomimetically activated amino acids.

The availability of only a few , β-lactamase inhibitor compounds however, is insufficient to counter the constantly increasing diversity of β-lactamases for which a variety of novel and distinct inhibitors has become a necessity. There is, therefore, a need for the ability to identify new β-lactamase inhibitors. The development of fully synthetic inhibitors would greatly facilitate meeting this need. Ideally, certain embodiments of such inhibitors would also bind bacterial DD-peptidases, thus potentially acting both as β-lactamase inhibitors and as antibiotic agents.

BRIEF SUMMARY OF THE INVENTION

The invention provides novel β-lactamase inhibitors, which are structurally unrelated to the natural product and semi-synthetic β-lactamase inhibitors presently available, and which do not possess β-lactam pharmacophore. These new inhibitors are preferably fully synthetic, allowing ready access to a wide variety of structurally related analogs. Certain embodiments of these new inhibitors also bind bacterial DD-peptidases, and thus potentially act both as β-lactamase inhibitors and as antibiotics.

In a first aspect, the invention provides novel acylphosphate and acylphosphonate β-lactamase inhibitors. Preferably, such inhibitors have the general mixed anhydride structure of Formula I:

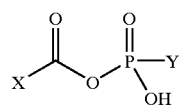

(I)

or salts thereof;

wherein X is alkyl, aryl, aralkyl, or heterocyclic radical; Y is Z or OZ; and Z is alkyl, aryl, aralkyl, acyl, heterocyclic radical, phosphonyl, or X; provided, however, that when Y is Z, then Z is not phosphonyl; and further provided that when Y is OZ and Z is phenyl, then X is not methyl or phenyl; when Y is OZ and Z is alkyl or adenosyl, then X is not an amino acid; and when Y is OZ and Z is benzoyl, then X is not phenyl.

In certain preferred embodiments, the mixed anhydride is an acylphosphate, and Y is thus OZ. In certain other preferred embodiments, the mixed anhydride is an acylphosphonate, and Y is thus Z.

In certain preferred embodiments, Y and X are taken together with the remaining atoms of the chain to form a cyclic structure of Formula II:

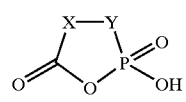

(II)

wherein Y is O or alkylene and X is alkylene, cycloalkylene, fused heterocycle, heteroarylene, or arylene, and wherein the alkylene, cycloalkylene, fused heterocycle, heteroarylene, and arylene groups may be optionally substituted; provided that X is not phenylethene.

In a second aspect, the invention provides pharmaceutical compositions comprising an acylphosphate or acylphosphonate β-lactamase inhibitor and a pharmaceutically acceptable carrier, excipient, or diluent. Preferably, such inhibitors have the general mixed anhydride structure (I):

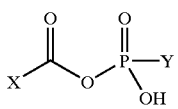

or salts thereof;
wherein X is alkyl, aryl, aralkyl, or heterocyclic radical; Y is Z or OZ; and Z is alkyl, aryl, aralkyl, acyl, heterocyclic radical, phosphonyl, or X; provided that when Y is Z, then Z is not phosphonyl.

In certain preferred embodiments, the mixed anhydride is an acylphosphate, and Y is thus OZ. In certain other preferred embodiments, the mixed anhydride is an acylphosphonate, and Y is thus Z.

In certain preferred embodiments, Y and X are taken together with the remaining atoms of the chain to form a cyclic structure of Formula II:

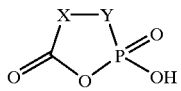

wherein Y is O or alkylene and X is alkylene, cycloalkylene, fused heterocycle, heteroarylene, or arylene, and wherein the alkylene, cycloalkylene, fused heterocycle, heteroarylene, and arylene groups may be optionally substituted.

In a third aspect, the invention provides methods for inhibiting in vitro or in vivo β-lactamase activity, such methods comprising administering an acylphosphate or acylphosphonate β-lactamase inhibitor. Preferably, such inhibitors have the general mixed anhydride structure of Formula I:

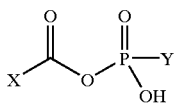

or salts thereof;
wherein X is alkyl, aryl, aralkyl, or heterocyclic radical; Y is Z or OZ; and Z is alkyl, aryl, aralkyl, acyl, heterocyclic radical, phosphonyl, or X; provided that when Y is Z, then Z is not phosphonyl.

In certain preferred embodiments, the mixed anhydride is an acylphosphate, and Y is thus OZ. In certain other preferred embodiments, the mixed anhydride is an acylphosphonate, and Y is thus Z.

In certain preferred embodiments, X and Y are taken together with the remaining atoms of the chain to form a cyclic structure of Formula II:

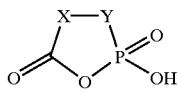

wherein Y is O or alkylene and X is alkylene, cycloalkylene, fused heterocycle, heteroarylene, or arylene, and wherein the alkylene, cycloalkylene, fused heterocycle, heteroarylene, and arylene groups may be optionally substituted In a fourth aspect, the invention provides a method for inhibiting bacterial growth, the method comprising administering an acylphosphate or acylphosphonate β-lactamase inhibitor. Preferably, such inhibitors have the general mixed anhydride structure of Formula I:

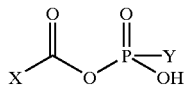

or salts thereof;
wherein X is alkyl, aryl, aralkyl, or heterocyclic radical; Y is Z or OZ; and Z is alkyl, aryl, aralkyl, acyl, heterocyclic radical, phosphonyl, or X; provided that when Y is Z, then Z is not phosphonyl.

In certain preferred embodiments, the mixed anhydride is an acylphosphate, and Y is thus OZ. In certain other preferred embodiments, the mixed anhydride is an acylphosphonate, and Y is thus Z.

In certain preferred embodiments, X and Y are taken together with the remaining atoms of the chain to form a cyclic structure of Formula II:

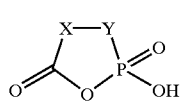

wherein Y is O or alkylene and X is alkylene, cycloalkylene, fused heterocycle, heteroarylene, or arylene, and wherein the alkylene, cycloalkylene, fused heterocycle, heteroarylene, and arylene groups may be optionally substituted In one embodiment of such a method, a β-lactamase inhibitor according to the invention is co-administered with an antibiotic. In another embodiment the β-lactamase inhibitor according to the invention has antibiotic activity, and can thus either be administered alone or be co-administered with another antibiotic agent.

DETAILED DESCRIPTION OF THE PREFERRED EMBODIMENTS

The invention relates to bacterial antibiotic resistance. More particularly, the invention relates to compositions and methods for overcoming bacterial antibiotic resistance. The patents and publications identified in this specification are within the knowledge of those skilled in this field and are hereby incorporated by reference in their entirety.

The invention provides novel β-lactamase inhibitors, which are structurally unrelated to the natural product and semi-synthetic β-lactamase inhibitors presently available, and which do not possess a β-lactam pharmacophore. These new inhibitors are preferably fully synthetic, allowing ready access to a wide variety of structurally related analogs. Certain embodiments of these new inhibitors also bind bacterial DD-peptidases, and thus potentially act both as β-lactamase inhibitors and as antibiotics.

For purposes of the present invention, the following definitions will be used:

As used herein, the term "β-lactamase" denotes a protein capable of inactivation of a β-lactam antibiotic. In one preferred embodiment, the β-lactamase is an enzyme which catalyzes the hydrolysis of the β-lactam ring of a β-lactam antibiotic. In certain preferred embodiments, the β-lactamase is microbial. In certain preferred embodiments, the β-lactamase is a serine β-lactamase. In certain other preferred embodiments, the β-lactamase is a zinc β-lactamase. The terms "class A", "class B", "class C", and "class D" β-lactamases are understood by those skilled in the art and can be found described in Waley, *The Chemistry of β-Lactamase*, Page Ed., Chapman & Hall, London, (1992) 198–228. In particularly preferred embodiments, the β-lactamase is class C β-lactamase of *Enterobacter cloacae* P99 (hereinafter P99 β-lactamase), or class A β-lactamase of the TEM-2 plasmid (hereinafter TEM β-lactamase).

As used herein, the term "β-lactamase inhibitor" is used to identify a compound having a structure as defined herein, which is capable of inhibiting β-lactamase activity. Inhibiting β-lactamase activity means inhibiting the activity of a class A, B, C, or class D β-lactamase. Preferably, such inhibition should be at a 50% inhibition concentration below 100 micrograms/ml, more preferably below 30 micrograms/ml and most preferably below 10 micrograms/ml.

In some embodiments of the invention, the β-lactamase inhibitor is also capable of acting as an antibiotic, for example, by inhibiting bacterial cell-wall cross-linking enzymes. Thus, the term β-lactamase inhibitor is intended to encompass such dual-acting inhibitors. In certain preferred embodiments, the β-lactamase inhibitor is capable of inhibiting D-alanyl-D-alanine-carboxy-peptidases/transpeptidases (hereinafter DD-peptidases). The term "DD-peptidase" is used in its usual sense to denote penicillin-binding proteins involved in bacterial cell wall biosynthesis (e.g., Ghysen, Prospect. Biotechnol.128:67–95 (1987)). In certain particularly preferred embodiments, the D-alanyl-D-alanine-carboxy-peptidases/transpeptidase inhibited is the Streptomyces R61 DD-peptidase.

The term "alkyl" as employed herein refers to straight and branched chain aliphatic groups having from 1 to 12 carbon atoms, preferably 1–8 carbon atoms, which may be optionally substituted with one, two or three substituents. Unless otherwise specified, the alkyl group may be saturated, unsaturated, or partially unsaturated. As used herein, therefore, the term "alkyl" is specifically intended to include alkenyl and alkynyl groups, as well as saturated alkyl groups. Preferred alkyl groups include, without limitation, methyl, ethyl, propyl, isopropyl, butyl, tert-butyl, isobutyl, pentyl, hexyl, vinyl, allyl, isobutenyl, ethynyl, and propynyl.

The term "alkylene" as employed herein refers to saturated, unsaturated, and partially unsaturated groups having from 1 to 8 carbon atoms, preferably 1–6 carbon atoms, more preferably 1–4 carbon atoms, and most preferably 1–2 carbon atoms, positioned between and connecting two other substituents. Preferred alkylene groups include, without limitation, methylene, ethylene, and ethene. For purposes of the invention, an alkylene group preferably refers to a portion of a cyclic structure.

As employed herein, a "substituted" alkyl, cycloalkyl, aryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, amino, alkylcarboxamido, arylcarboxamido, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, cyano, and alkylaminocarbonyl groups.

The term "cycloalkyl" as employed herein includes saturated and partially unsaturated cyclic hydrocarbon groups having 3 to 12, preferably 3 to 8, more preferably 3 to 6 carbons, wherein one or two ring positions may be substituted with an oxo group, and wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexanone, cycloheptyl, and cyclooctyl. A "cycloalkylene" group is a cycloalkyl group positioned between and connecting two other substituents. Preferred cycloalkylene groups include, without limitation, cyclohexylene, cyclopentylene, and cyclobutylene.

An "aryl" group is a $C_6$–$C_{14}$ aromatic moiety comprising one to three aromatic rings, which may be optionally substituted. Preferably, the aryl group is a $C_6$–$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $C_{1-6}$alk($C_{6-10}$)aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, and methylnaphthyl.

An "arylene" group is a $C_{6-10}$ aryl group positioned between and connecting two other substituents. The arylene group may be optionally substituted. A non-limiting example of an arylene group is phenylene. For purposes of the invention, the arylene group preferably constitutes one ring of a fused bicyclic or tricyclic ring system.

A "heterocyclic" group or radical is a ring structure having from about 3 to about 8 atoms, wherein one or more atoms are selected from the group consisting of N, O, and S. The heterocyclic group may be optionally substituted on carbon with oxo or with one of the substituents listed above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino.

In certain preferred embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, between one and about three heteroatoms selected from the group consisting of N, O, and S. Preferred heteroaryl groups include, without limitation, thienyl, benzothienyl, furyl, benzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl. In certain other preferred embodiments, a heterocyclic group is fused to an aryl or heteroaryl group. Examples of such fused heterocycles include, without limitation, tetrahydroquinoline and dihydrobenzofuran.

A "heteroarylene" group is a heteroaryl group positioned between and connecting two other groups. The heteroarylene group may be optionally substituted. For purposes of the invention, the heteroarylene group preferably forms one ring of a fused bicyclic or tricyclic ring system.

The term "halogen" or "halo" as employed herein refers to chlorine, bromine, fluorine, or iodine.

As herein employed, the term "acyl" refers to an alkylcarbonyl or arylcarbonyl substituent, wherein the alkyl or aryl portion may be optionally substituted.

The term "amido" as employed herein refers to a formylamino, alkylcarbonylamino, or arylcarbonylamino group. The term "amino" is meant to include $NH_2$, alkylamino, arylamino, and cyclic amino groups.

The term "phosphate" refers to groups in which there are four oxygen atoms around a phosphorous atom. The term "phosphonate" refers to groups in which there are three oxygen atoms around a phosphorous atom. The term "phosphonyl" refers to a radical in which there are three oxygen atoms around a phosphorous atom. The phosphonyl radical may be attached to carbon to form a phosphonate group or to oxygen to form a phosphate group.

In a first aspect, the invention provides novel acylphosphate and acylphosphonate β-lactamase inhibitors. Preferably, such inhibitors have the general mixed anhydride structure (I):

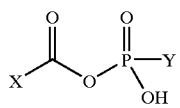

(I)

or salts thereof;

wherein X is alkyl, aryl, aralkyl, or heterocyclic radical; Y is Z or OZ; and Z is alkyl, aryl, aralkyl, acyl, heterocyclic radical, phosphonyl, or X; provided, however, that when Y is Z, then Z is not phosphonyl; and further provided that when Y is OZ and Z is phenyl, then X is not methyl or phenyl; when Y is OZ and Z is alkyl or adenosyl, then X is not an amino acid; and when Y is OZ and Z is benzoyl, then X is not phenyl. Particularly preferred values for X are Ph, C(O)Ph, and Me. Particularly preferred values for Z are Ph, C(O)Ph, Me, and $PO_3C(O)Ph$.

In certain preferred embodiments, the mixed anhydride is an acylphosphate, and Y is thus OZ. In these embodiments, Z is preferably phenyl or C(O)Ph and X is preferably Ph.

In certain other preferred embodiments, the mixed anhydride is an acylphosphonate, and Y is thus Z. Preferably in these embodiments, X and Z are each Ph.

In certain preferred embodiments, Y and X are taken together with the remaining atoms of the chain to form a cyclic structure of Formula II:

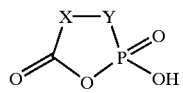

(II)

wherein Y is O or alkylene, and X is alkylene, cycloalkylene, fused heterocycle, heteroarylene, or arylene, wherein the alkylene, cycloalkylene, fused heterocycle, heteroarylene, and arylene groups may be optionally substituted; provided that X is not phenylethene. In certain preferred embodiments, X is a fused carbocyclic, heterocyclic, aromatic, or heteroaromatic ring. In one such preferred embodiment, X is phenylene, giving the structure of Formula III:

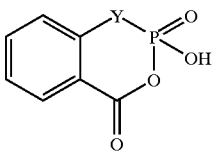

(III)

wherein Y is O, or alkylene.

The compounds according to this aspect of the invention are useful as β-lactamase inhibitors. In certain preferred embodiments, the compounds of the invention also have utility as antibiotic agents. Furthermore, the inhibitors of the invention are also useful as probes for elucidating and identifying mechanisms responsible for bacterial antibiotic resistance and for evaluating the effect of administering agents to overcome such resistance concomitantly with antibiotic treatments.

Nonlimiting examples of certain preferred embodiments according to the invention appear in Table 1. These examples are shown as salts. It would be evident to one skilled in the art that the compounds of Formulae I-III can exist in conjugate acid, conjugate base, or salt form. The disclosure of compounds, compositions, and methods contained herein is, in each instance, expressly intended to include all such forms.

TABLE 1

| | |
|---|---|
| IV | 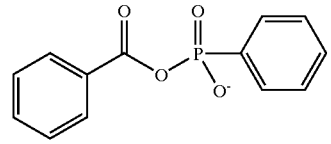 |
| V | 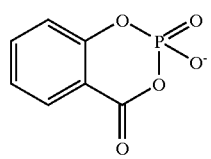 |
| VI | 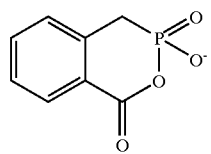 |
| VII | 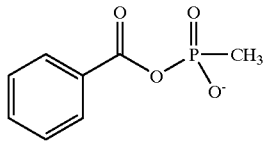 |
| VIII | 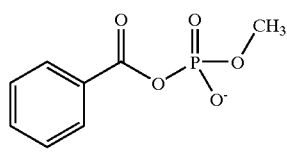 |

TABLE 1-continued

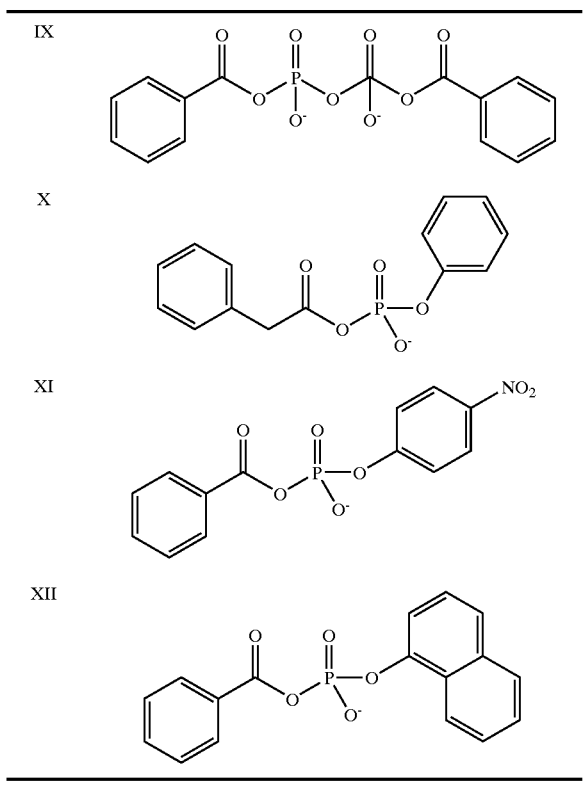

In a second aspect, the invention provides pharmaceutical compositions comprising an acylphosphate or acylphosphonate β-lactamase inhibitor and a pharmaceutically acceptable carrier, excipient, or diluent. Preferably, such inhibitors have the general mixed anhydride structure (I):

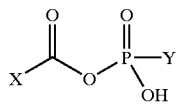

(I)

or salts thereof;
wherein X is alkyl, aryl, aralkyl, or heterocyclic radical; Y is Z or OZ; and Z is alkyl, aryl, aralkyl, acyl, heterocyclic radical, phosphonyl, or X; provided that when Y is Z, then Z is not phosphonyl.

In certain preferred embodiments, the mixed anhydride is an acylphosphate, and Y is thus OZ. In certain other preferred embodiments, the mixed anhydride is an acylphosphonate, and Y is thus Z.

In certain preferred embodiments, Y and X are taken together with the remaining atoms of the chain to form a cyclic structure of Formula II:

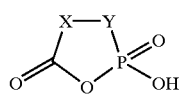

(II)

wherein Y is O or alkylene and X is alkylene, cycloalkylene, fused heterocycle, heteroarylene, or arylene, and wherein the alkylene, cycloalkylene, fused heterocycle, heteroarylene, and arylene groups may be optionally substituted. In certain preferred embodiments, X is a fused carbocyclic, heterocyclic, aromatic, or heteroaromatic ring.

In one such preferred embodiment, X is phenylene, giving the structure of Formula III:

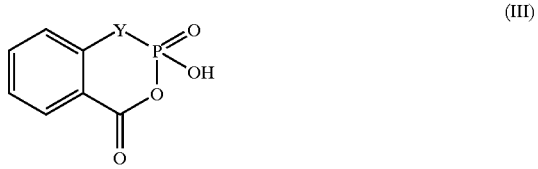

(III)

wherein Y is O or alkylene.

The characteristics of the carrier, excipient, or diluent will depend on the route of administration. As used herein, the term "pharmaceutically acceptable" means a non-toxic material that does not interfere with the effectiveness of the biological activity of the active ingredient(s). The term "physiologically acceptable" refers to a non-toxic material that is compatible with a biological system such as a cell, cell culture, tissue, or organism. Preferably, the biological system is a living organism, more preferably a mammal, most preferably a human. Thus compositions and methods according to the invention, may contain, in addition to the inhibitor, diluents, fillers, salts, buffers, stabilizers, solubilizers, and other materials well known in the art.

In certain preferred embodiments, the pharmaceutical compositions according to this aspect of the invention additionally comprise an antibiotic agent. In particularly preferred embodiments, the antibiotic agent is a β-lactam antibiotic. The pharmaceutical composition of the invention may also contain other active factors and/or agents which enhance inhibition of β-lactamase and/or DD-peptidases.

The term "antibiotic" is used herein to describe a composition which decreases the viability or which inhibits the growth or reproduction of microorganisms. As used in this disclosure, an antibiotic is further intended to include an antimicrobial, bacteriostatic, or bactericidal agent. Non-limiting examples of antibiotics useful according to this aspect of the invention include penicillins, cephalosporins, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and others. The term "β-lactam antibiotic" is used to designate compounds with antibiotic properties containing a β-lactam functionality. Non-limiting examples of β-lactam antibiotics useful according to this aspect of the invention include penicillins, cephalosporins, penems, carbapenems, and monobactams.

In certain preferred embodiments, the second aspect of the invention provides pharmaceutical compositions for use in the methods of the invention.

In a third aspect, the invention provides methods for inhibiting in vitro or in vivo β-lactamase activity, such methods comprising administering an acylphosphate or acylphosphonate β-lactamase inhibitor. Preferably, such inhibitors have the general mixed anhydride structure of Formula I:

(I)

or salts thereof;
wherein X is alkyl, aryl, aralkyl, or heterocyclic radical; Y is Z or OZ; and Z is alkyl, aryl, aralkyl, acyl, heterocyclic radical, phosphonyl, or X; provided that when Y is Z, then Z is not phosphonyl.

In certain preferred embodiments, the mixed anhydride is an acylphosphate, and Y is thus OZ. In certain other preferred embodiments, the mixed anhydride is an acylphosphonate, and Y is thus Z.

In certain preferred embodiments, X and Y are taken together with the remaining atoms of the chain to form a cyclic structure of Formula II:

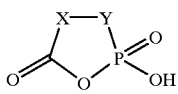

(II)

wherein Y is O or alkylene and X is alkylene, cycloalkylene, fused heterocycle, heteroarylene, or arylene, and wherein the alkylene, cycloalkylene, fused heterocycle, heteroarylene, and arylene groups may be optionally substituted. In certain preferred embodiments, X is a fused carbocyclic, heterocyclic, aromatic, or heteroaromatic ring. In one such preferred embodiment, X is phenylene, giving the structure of Formula III:

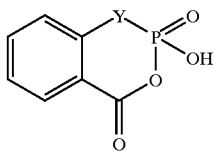

(III)

wherein Y is O or alkylene.

Non-limiting examples of particularly preferred inhibitors to be used according to this aspect of the invention are shown in Table 2.

TABLE 2-continued

XVI
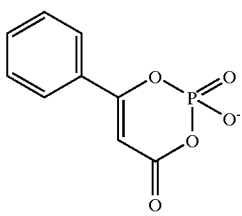

In a fourth aspect, the invention provides a method for inhibiting bacterial growth, the method comprising administering an acylphosphate or acylphosphonate β-lactamase inhibitor. Preferably, such inhibitors have the general mixed anhydride structure of Formula I:

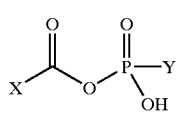

(I)

or salt thereof;
wherein X is alkyl, aryl, aralkyl, or heterocyclic radical; Y is Z or OZ; and Z is alkyl, aryl, aralkyl, acyl, heterocyclic radical, phosphonyl, or X; provided that when Y is Z, then Z is not phosphonyl.

In certain preferred embodiments, the mixed anhydride is an acylphosphate, and Y is thus OZ. In certain other preferred embodiments, the mixed anhydride is an acylphosphonate, and Y is thus Z.

In certain preferred embodiments, X and Y are taken together with the remaining atoms of the chain to form a cyclic structure of Formula II:

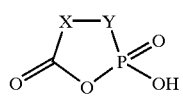

(II)

wherein Y is O or alkylene and X is alkylene, cycloalkylene, fused heterocycle, heteroarylene, or arylene, and wherein the alkylene, cycloalkylene, fused heterocycle, heteroarylene, and arylene groups may be optionally substituted. In certain preferred embodiments, X is a fused carbocyclic, heterocyclic, aromatic, or heteroaromatic ring. In one such preferred embodiment, X is phenylene, giving the structure of Formula III:

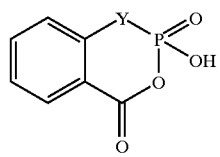

(III)

wherein Y is O or alkylene.

The methods according to this aspect of the invention are useful for inhibiting bacterial growth in a variety of contexts. For example, such methods can be used to prevent the growth of β-lactam resistant bacteria in experimental cell cultures. Such methods can also be used to prevent the growth of β-lactam resistant bacteria in veterinary contexts. In addition, such methods can be used to prevent the growth of β-lactam resistant bacteria in human patients.

Accordingly, in a preferred embodiment of this aspect, the invention provides methods for inhibiting bacterial growth in an animal, including a human, comprising the step of administering a therapeutically effective amount of β-lactamase inhibitors according to the invention for a therapeutically effective period of time to the animal.

The terms "therapeutically effective amount" and "therapeutically effective period of time" are used to denote known treatments at dosages and for periods of time effective to show a meaningful patient benefit, i.e., healing of conditions associated with bacterial infection, and/or bacterial drug resistance. The β-lactamase inhibitors of the invention may be administered to the animal by any route, including parenterally, orally, sublingually, transdermally, topically, intranasally, intratracheally, or intrarectally. When administered systemically, the therapeutic composition is preferably administered at a sufficient dosage to attain a blood level of inhibitor from about 0.1 µg/mL to about 1 mg/mL, more preferably from about 0.1 µg/mL to about 100 µg/mL, and most preferably from about 0.1 µg/mL to about 10 µg/mL. For localized administration, much lower concentrations than this may be effective, and much higher concentrations may be tolerated. In a preferred embodiment, the inhibitor is administered orally.

In certain preferred embodiments of the method according to this aspect of the invention, a β-lactamase inhibitor according to the invention is co-administered with an antibiotic. In a particularly preferred embodiment of the invention, the co-administered antibiotic is a β-lactam antibiotic. For purposes of this invention, the term "co-administered" is used to denote sequential or simultaneous administration. In certain other preferred embodiments, the β-lactamase inhibitor according to the invention has antibiotic activity, and thus either can be administered alone or can be co-administered with a β-lactam antibiotic or any other type of antibiotic. In some embodiments, more than one β-lactamase inhibitor may be administered sequentially or simultaneously.

The following examples are intended to further illustrate certain preferred embodiments of the invention, and are not intended to limit the scope of the invention.

EXAMPLE 1

Chemical Synthesis of β-lactamase Inhibitors

Representative acylphosphate and acylphosphonate inhibitors having structures IV and VII-XV according to the present invention were synthesized according to standard protocols. The following paragraphs set forth available synthetic approaches according to methods known in the art.

The inhibitor of structure XIII (sodium benzoyl phenyl phosphate) was prepared according to standard methods (e.g., by a modification of the method employed by Jencks, et al. J. Biol. Chem. 234: 1272–1279 (1959)) for the synthesis of acetyl phenyl phosphate. Thus, to a solution of 2.0 g (7.8 mmol) of disodium phenyl phosphate (Adrich Chemical Co.) in 15 ml of water, cooled in an ice bath, was added 3.5 g (15.8 mmole) of benzoic anhydride (Acros Organics) dissolved in 10 ml pyridine, dropwise with stirring. After 25 min., the reaction mixture was extracted three times with diethyl ether and the aqueous phase then freeze-dried. The solid residue was recrystallized twice from water and characterized by NMR spectra.

The inhibitor having structure IV (sodium benzoyl phenylphosphonate) was synthesized using the procedure of Laird et al. J. Chem. Soc. Perkin II, 1434–1436 (1973), to yield the diester, dibenzoyl phenylphosphonate, m.p. 104–106° C. (recrystallized from acetonitrile) which was dissolved in 1:1 acetone/water and titrated to a stable pH 7.0 endpoint over 30 min. with sodium bicarbonate. Acetone was then removed by rotary evaporation and the residual aqueous solution freeze-dried. The required product was purified by elution with water from Biorad P-2 column.

The inhibitor having structure XIV (sodium dibenzoyl phosphate) was prepared in an analogous fashion to the inhibitor having structure XIII, beginning with disodium hydrogen phosphate and benzoic anhydride in a 1:2 molar ratio. The product was recrystallized twice from water, with final melting point 195–197° C.

The inhibitors having structures X, XI, and XII were also prepared in an analogous fashion to the inhibitor having structure XIII, and were characterized as follows:

Compound X: $^1$H NMR ($^2$H$_2$O): δ 3.83 (s, 2H), 6.99 (d, J=8.3 Hz, 2H), 7.20 (t, J=7.4 Hz, 1H), 7.3–7.5 (m, 7H); $^{31}$P ($^2$H$_2$O): δ −15.2.

Compound XI: $^1$H NMR ($^2$H$_2$O): δ 7.43 (d, J=8.7 Hz, 2H), 7.56 (t, J=7.9 Hz, 2H), 7.74 (t, J=7.4 Hz, 1H), 8.07 (d, J=7.6 Hz, 2H), 8.29 (d, J=8.9 Hz, 2H); $^{31}$P ($^2$H$_2$O): δ −15.6.

Compound XII: $^1$H NMR ($^2$H$_2$O): δ 7.41 (d, J=8 Hz, 1H), 7.51 (m, 4 H), 7.67 (m, 2H), 7.83 (d, J=8 Hz, 1H), 7.91 (d, J=8 Hz, 2H), 8.02 (d, J=2H).

The representative cyclic acylphosphate and cyclic acylphosphonate inhibitors having structures V, VI, and XVI according to the present invention were synthesized according to standard protocols. The following paragraphs set forth possible synthetic approaches, according to methods known in the art.

The acylphosphate 1-hydroxy-4.5-benz-2.6-dioxaphosphorinanone-(3)-i-oxide were synthesized by the hydrolysis of 1-chloro4.5-benz-2.6-dioxaphosphorinanone-(3)-1-oxide according to standard methods (e.g., Bruice et al., J. Am. Chem. Soc. 117:12064–12069 (1995). Salicylic acid (69.0 g) and phosphorus oxychloride (76.7 g) were gradually heated to 150 ° C. for 2 hours. The viscous product was distilled and the fraction b.p. 116–125 ° C./0.02 mm. collected and crystallized from carbon tetrachloride according to standard methods (e.g., Montgomery et al. J Chem Soc 4603–4606 (1956)).

After a preparative scale hydrolysis, the inhibitor of structure V was isolated and characterized as a stable dicyclohexylamine salt. The cyclic phosphoryl chloride (500 mg; 2.3 mmol) was suspended in 60 mL of anhydrous acetonitrile (Aldrich, Sure/Seal) and water (41 μL, 2.3 mmol) added with magnetic stirring. The mixture was then gently warmed until the crystals of the starting material disappeared (ca. 5 min.). Two molar equivalents of redistilled dicyclohexylamine (913 μL) were then added. The immediately precipitating solid (cyclohexylamine hydrochloride) was removed by vacuum filtration and the remaining solvent by rotary evaporation. The residual colorless solid was recrystallized from acetonitrile/diethyl ether yielding 310 mg (35%) of the required product. (Characterization: mp 160–163° C.; $^1$H NMR ($^2$H$_2$O): δ (aromatics) 7.27 (d, 1H, J=8 Hz), 7.35 (t, 1H, J=8 Hz), 7.78 (t, 1H, J=8 Hz), 8.05 (d, 1H, J=8 Hz); $^{31}$P ($^2$H$_2$O) δ −12.55; UV (20 mM MOPS buffer, pH 7.5) $\lambda_{max}$ 239 nm (ϵ=1.01× 10$^4$cm$^{-1}$M$^{-1}$), 295 nm (ϵ=2.52×10$^3$cm$^{-1}$M$^{-1}$); IR (KBr) 1737 cm$^{-1}$ (C=O), 1613 cm$^{-1}$ (C=C), 1286 cm$^{-1}$ (P=O); Anal. Calcd. for C$_{19}$H$_{28}$NO$_5$P: C, 59.80; H, 7.40; N, 3.67; P, 8.12. Found: C, 60.11; H, 7.44; N, 3.70; P, 7.91.). The cyclic phosphate hydrolyzed slowly in buffer at neutral pH. The rate of hydrolysis—k$_{obs}$=1.7×10$^{-5}$s$^{-1}$ in 20 mM MOPS, pH 7.5, 25° C.—is in accord with literature values. Kintetics were determined spectrophotometrically at 240 nm, and an isosbestic point for the hydrolysis of salicyl phosphate to salicylate was observed.

The cyclic acyl phosphate inhibitor having structure XVI was synthesiszed according to the published procedure (Marecek and Griffith, J. Am. Chem. Soc. 92:917 (1970)).

The representative cyclic acyl phosphonate inhibitor having structure VI was synthesized by thermal hydration of the corresponding acyclic diacid by heating up to 150° C.

EXAMPLE 2

In Vitro Inhibition of β-Lactamase and of DD-Peptidase

To evaluate the inhibitors and the methods of the invention, representative inhibitors preparations were tested using class A (TEM-2 plasmid TEM)) β-lactamase and class C (*Enterobacter cloacae* P99 β-lactamase) β-lactamases (Porton Down, Wiltshire, U.K.) as well as representative DD-peptidases/carboxydases (e.g., Streptomyces R61 DD-peptidases) as the assayed enzyme.

Steady state kinetic parameters were directly obtained for representative inhibitors with the P99 β-lactamase with TEM β-lactamase by standard methods (e.g., Wilkinson, Biochem J. 80:324–332 (1989)) from spectrophotometric initial velocity measurements. Kinetic parameters were also obtained for DD-peptidase as the assayed enzyme, according to standard methods using hyppuryl-DL-phenyl-lactate (a known DD-peptidase substrate) (e.g. Govardhan and Pratt, Biochemistry 26:3385–3395 (1987)). The concentration of stock enzyme solutions were determined spectrophotometrically (e.g., Xu, et al., Biochemistry 35:3595–33603 (1996)).

Representative class C and a class A β-lactamases were inhibited by representative inhibitors of Formulae I and II in a time-dependent fashion as described by the relation:

where K$_i$ (s$^{-1}$M$^{-1}$) represents the second order rate constant for inhibition of assayed enzymes upon treatment with the inhibitors according to the present invention.

Representative inhibitors of the invention having Formula I may act by forming a covalent bond between β-lactamases and the inhibitor (i.e., irreversible inhibition). This type of inhibition is therefore time dependent. It is distinguished from reversible inhibition in so far that the backward reaction is extremely slow. Kinetically, irreversible inhibition is inhibition in which the inhibitor does not significantly dissociate from the enzyme within the experimental time frame. Thus, irreversible inhibition is measured by how fast the event takes place (rate constant k$_i$). Thus, inhibitory efficiency is expressed by large k$_i$ values.

Representative inhibitors of Formula I may also act by forming a transient acyl-enzyme intermediate. Inhibition results from a slow turn over (de-acylation) of the intermediate. Hence, inhibition is by the second order rate constant for the formation of the acyl-enzyme intermediate (i.e., k$_{cat}$/K$_m$). Notably, an inhibitor according to the present invention may inhibit according to both mechanisms as illustrated for example by the inhibitor having structure VII, for which both k$_{cat}$/K$_m$ and k$_i$ values are reported.

Representative β-lactamase inhibition test results for inhibitors of the invention are shown in Table 3. In Table 3, k$_{cat}$/K$_m$ values are presented in plain text, with k$_i$ values for representative inhibitors appearing in parentheses. The data in Table 3 also show that some inhibitors of the invention (e.g., inhibitors having structures V and VII) may have antibiotic properties, as evidenced by their inhibition of DD-peptidase.

TABLE 3

| No. | Inhibitor Structure | $k_i$ (s$^{-1}$ M$^{-1}$) and $k_{cat}/k_m$ (s$^{-1}$ M$^{-1}$) | | |
|---|---|---|---|---|
| | | *Enterobacter cloacae* P99 β-lactamase | TEM-2 plasmid (TEM) | DD-peptidase |
| VII | | 66.7 (6.0) | | (0.2) |
| XIII | | 6070 (–) | 10 (0.2) | |
| IV | | 6900 (70) | 1.9 (1.6) | |
| XIV | | 3950 (–) | 1200 (14.3) | |
| V | | 5.6 × 10³ | 13.8 | 0.46 |
| positive control | clavulanic acid | 4 | 4.8 × 10⁴ | |

EXAMPLE 3

Inhibition of P99 β-lactamase

The enzyme (*Enterobacter cloacae* P99 β-lactamase) was dissolved to a concentration of 1 mg/mL in 20 mM MOPS buffer at pH 7.50, and then diluted 200-fold in the same buffer containing 0.1% BSA. The commercially available substrate nitrocefin was added as a 100 μM stock solution in 20 mM MOPS buffer, and inhibitors were also added as solutions in MOPS buffer. In a typical assay the following amounts were used: 300 μL of nitrocefin, 10 μL of P99 β-lactamase, xμL of inhibitor, and 110μL of MOPS buffer. Enzyme activity was measured at 25 °C., and the reaction was monitored spectrophotometrically at 482 nm. IC$_{50}$ values were determined from the dose-response plots of the initial reaction rate vs. inhibitor concentration. Results are presented in Table 4.

TABLE 4

| No. | Inhibitor Structure | IC$_{50}$ (μM) P99 β-lactamase |
|---|---|---|
| X | 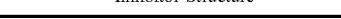 | 30 |

TABLE 4-continued

| No. | Inhibitor Structure | IC$_{50}$ ($\mu$M) P99 $\beta$-lactamase |
|-----|---------------------|------------------------------------------|
| XI  |                     | 39                                       |
| XII |                     | 8                                        |

EXAMPLE 4

Microbiological Testing

To test the inhibitors of the invention, a wide range of organisms are used to assess compounds according to the invention both as antibiotics and as β-Lactamase inhibitors: Initial screening for antibiotic activity utilizes penicillin sensitive *S. aureus* [ATTC# 25923], ampicillin sensitive *H. influenzae* [ATCC#10211] and clinical laboratory isolates of ampicillin sensitive *E. faecalis* and *H. influenzae*, and non-resistant *P. aeruginosa*. Initial studies utilize, in microtiter wells, 1 microgram of compound in 10 microliters diluted stock solution, 41,100 CFU of bacteria in 10 microliters broth solution and 80 microliters CAMHB. The count verification well contains 10 microliters CAMHB in place of the test compound. Tests for β-Lactamase inhibition utilize 1:1 and 1:10 wt/wt ratios of β-Lactam/ β-Lactamase inhibitor (10 micrograms/ml β-Lactam) and initially utilize penicillinase-producing *S. aureus* [ATTC# 29213] with piperacillin, extended-spectrum lactamase-producing *Klebsiella oxytoca* [ATCC# 51983] with piperacillin or ticarcillin, cephalosporinase-producing *E. cloace* [ACC# 23355] with cefoxitin or ceftriaxone, broad -spectrum lactamase-producing *E. coli* [ATCC# 35218] with amoxicillin, piperacillin or ticarcillin, broad-spectrum lactamase-producing *N. gonnorhea* [ATTC# 49226] with amoxicillin, lactamase-producing *H. influenzae* [ATTC# 43163] with tricarcillin, and lactamase-producing *E. faecalis* [ATTC# 49757] with amoxicillin. Microbiological and enzymatic testing is carried on duplicate plates with negative control plates.

Bacterial susceptibility may also be assayed by the gradient plate (i.e., the Kirby-Bauer) method. (*Microbiology: Including Immunology and Molecular Genetics* (3rd ed.) (Davis et al. eds.(1980) J.P. Lippincott Co., Philadelphia, Pa.). Briefly, according to this method standard filter paper disks impregnated with fixed amounts of compositions of inhibitors, ranging from 100 μg/ml to 1 mg/ml and from 10 μg /ml to 100 μg/ml and of inhibitors as well as antibiotic are dried. A "lawn" of bacteria is seeded on the surface of an agar LB plate (see e.g., *Molecular Cloning* 2nd edition, Cold Spring Harbor Laboratory Press (1989)) in the presence of inhibitors concentrations with a swab moistened with a standardized liquid culture, and several different inhibitor compositions-impregnated on disks are placed on the surface of the agar. The plates are then incubated over-night and the diameter of the zone showing no growth is then measured. The diameter of this zone of inhibition will be used to determine the minimal inhibitory concentration (MIC) value for susceptibility of the organism under scrutiny has high, intermediate, or inadequate insensitivity to the drug tested. These assays are expected to show that the inhibitors of the invention are effective to render infecting microorganisms susceptible and thus that the compositions and methods of the invention are useful for overcoming bacterial antibiotic resistance.

Broth or agar dilution methods are also used to determine the MIC value for susceptibility of bacterial isolates to the inhibitors of the invention. Briefly described, tubes are inoculated to contain $10^4$ to $10^8$ organisms/ml or LB plates (supra) are inoculated with $10^3$ to $10^4$ organisms. Various concentrations of inhibitor compositions (and of clavulanic acid, as positive controls) are added to several individual plates or tubes, (no inhibitor is added to negative control plates or tubes). These assays are expected to identify MIC ranges comparable to those observed for clavulanic acid (see e.g., Bateson et al., Bioorg. & Med. Chem. Letts. 4: 1667–1672 (1994)).

Results of microbiological testing for compounds of the invention are presented in Table 5. Compounds were tested at a concentration of 100 μg/mL. Compounds not shown in the Table gave negative results in these assays.

In Table 5, the microorganism tested against is shown in italics, while the antibiotic agent used is shown in plain text. The symbol (+) means that the inhibitor of the invention showed biological activity, as determined by an increase in antibiotic activity of the antibiotic agent. When determined, the number in parentheses indicates the fold reduction in the MIC of the antibiotic agent when measured in the presence of the inhibitor of the invention. The symbol (−) means that the inhibitor of the invention showed no biological activity, i.e., the antibiotic efficacy of the antibiotic agent was unchanged in the presence of the inhibitor.

TABLE 5

| Compound | Ent. cloacae Ceftriaxone | Ent. cloacae Cefoxitin | Staph. aureaus Piperacillin | Haemophilus influenzae Ticarcillin |
|---|---|---|---|---|
| IV | + (2) | + (2) | – | – |
| V | – | – | + (2) | – |
| VII | + (2) | + (2) | – | + |
| VIII | + (2) | + (2) | – | + |
| XVI | – | – | + (2) | – |

Successful inhibition of bacterial β-Lactamase activity in these assays is expected to be predictive of success in animals and humans.

What is claimed is:

1. A β-lactamase inhibitor of Formula I

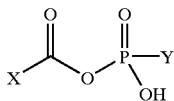
(I)

or a salt thereof;

wherein X is Ph, C(O)Ph, or Me; Y is Z or OZ; and Z is Ph, C(O)Ph, Me, or PO$_3$C(O)Ph.

2. The inhibitor according to claim 1, selected from the group consisting of:

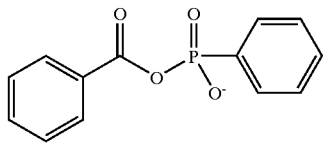

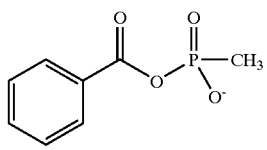

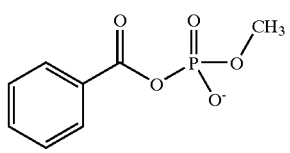

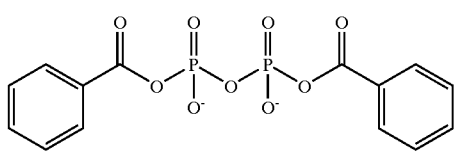

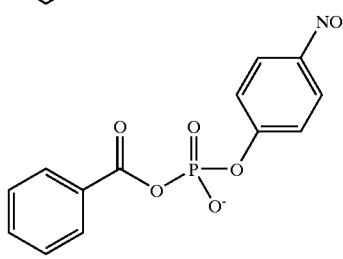

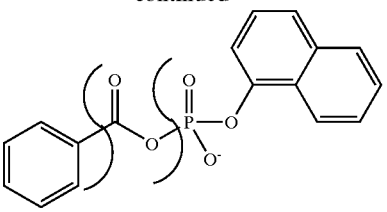

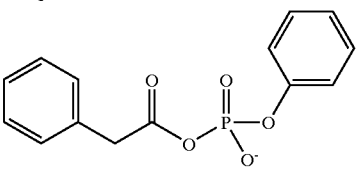

3. A pharmaceutical composition comprising a β-lactamase inhibitor of Formula I:

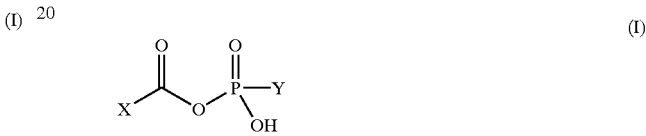
(I)

or a salt thereof;

wherein X is alkyl, alkenyl, alkynyl, aryl, aralkyl, or heterocyclic radical; Y is Z or OZ; and Z is alkyl, alkenyl, alkynyl, aryl, aralkyl, acyl, heterocyclic radical, phosphonyl, or X; provided, however, that when Y is Z, then Z is not phosphonyl; and further provided that when Y is Z and Z is methyl, then X is not methyl; and a pharmaceutically acceptable carrier, excipient, or diluent.

4. The composition according to claim 3, wherein X is Ph, C(O)Ph, or Me, and Z is Ph, C(O)Ph, Me, or PO$_3$C(O)Ph.

5. A pharmaceutical composition comprising a β-lactamase inhibitor of Formula I

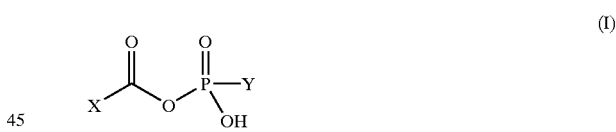
(I)

or a salt thereof wherein X is Ph, C(O)Ph, or Me, and Z; Y is Z or OZ; and Z is Ph, C(O)Ph, Me, or PO$_3$C(O)Ph; and a pharmaceutically acceptable carrier, excipient, or diluent.

6. A pharmaceutical composition comprising a β-lactamase inhibitor of Formula II

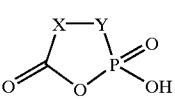
(II)

wherein Y is O or alkylene, and X is a fused carbocyclic, heterocyclic, aromatic, heteroaromatic ring or phenylene, wherein the fused carbocyclic, heterocyclic, aromatic, heteroaromatic ring or phenylene, may be optionally substituted.

* * * * *